US012233014B2

(12) United States Patent
Schreiber

(10) Patent No.: US 12,233,014 B2
(45) Date of Patent: Feb. 25, 2025

(54) MODULAR PATIENT LIFT SYSTEM

(71) Applicant: SLD Technology, Inc., Portland, OR (US)

(72) Inventor: Kevin Joseph Schreiber, Portland, OR (US)

(73) Assignee: SLD Technology, Inc., Portland, OR (US)

( * ) Notice: Subject to any disclaimer, the term of this patent is extended or adjusted under 35 U.S.C. 154(b) by 0 days.

(21) Appl. No.: 17/747,223

(22) Filed: May 18, 2022

(65) Prior Publication Data

US 2022/0370272 A1  Nov. 24, 2022

Related U.S. Application Data

(60) Provisional application No. 63/190,232, filed on May 18, 2021.

(51) Int. Cl.
*A61G 7/10* (2006.01)
(52) U.S. Cl.
CPC ........ *A61G 7/1042* (2013.01); *A61G 2203/30* (2013.01); *A61G 2203/36* (2013.01)
(58) Field of Classification Search
USPC ........................................ 702/185, 182, 183
See application file for complete search history.

(56) References Cited

U.S. PATENT DOCUMENTS

| 8,793,094 | B2 * | 7/2014 | Tam ...................... | H02P 25/032 |
| | | | | 702/56 |
| 11,186,989 | B2 * | 11/2021 | Schreiber ................ | E04B 9/006 |
| 2013/0246088 | A1 * | 9/2013 | Huster ............... | G06Q 10/0635 |
| | | | | 705/2 |
| 2013/0344795 | A1 * | 12/2013 | Schreiber .............. | F24F 13/078 |
| | | | | 454/295 |
| 2016/0235378 | A1 * | 8/2016 | Yun ........................ | H05G 1/025 |
| 2020/0085657 | A1 * | 3/2020 | Wiggermann .......... | B66C 13/16 |
| 2021/0236365 | A1 * | 8/2021 | Zilberman ............. | G16H 20/30 |
| 2021/0402044 | A1 * | 12/2021 | Chase .................. | A61G 13/108 |
| 2022/0142841 | A1 * | 5/2022 | Jelinek ................. | A61G 7/1015 |

FOREIGN PATENT DOCUMENTS

EP            2057976 A2 *  5/2009  .......... A61G 7/1042

* cited by examiner

*Primary Examiner* — Adam C Ortiz
(74) *Attorney, Agent, or Firm* — Evan R. Sotiriou; Burris Law, PLLC

(57) ABSTRACT

A modular patient lift system includes a ceiling grid, a plurality of rails, a gantry configured to traverse the ceiling grid via the plurality of rails, and a patient lift coupled to the gantry and configured to traverse the ceiling grid with the gantry. The modular patient lift system further includes one or more sensors provided on at least one of the plurality of rails, the gantry, and the patient lift, the one or more sensors configured to collect at least one of environmental data and position data.

19 Claims, 5 Drawing Sheets

MODULAR PATIENT LIFT SYSTEM

CROSS-REFERENCE TO RELATED APPLICATIONS

This non-provisional application claims the benefit of and priority to U.S. Provisional Application No. 63/190,232, filed May 18, 2021. The disclosure of the prior application is hereby incorporated by reference herein in its entirety.

BACKGROUND

Traditional patient lift systems require manual movement of a patient on a lift from an initial location to a final destination, such as an imaging table or surgical table. The manual movement typically requires either manually transporting the patient on the lift using one or more people, such as medical personnel, or moving the patient via turning a crank that is used to mechanically transfer the patient from the initial location to the final destination. Accordingly, due to limitations with the traditional patient lift systems, the process of transferring a patient can be cumbersome, error prone, and time consuming. Furthermore, the lift creates challenges in space, such as a surgical suite, where the lift is deployed due to its size and structure. Specifically, the lift can inhibit necessary airflow to the area in which it is deployed, which can lead to contamination of the area (e.g., reduced air quality).

SUMMARY

This Summary is provided to introduce a selection of concepts in a simplified form that are further described below in the Detailed Description. This Summary is not intended to identify key factors or essential features of the claimed subject matter, nor is it intended to be used to limit the scope of the claimed subject matter.

In various examples, a modular patient lift system comprises a ceiling grid, a plurality of rails, a gantry configured to traverse the ceiling grid via the plurality of rails, and a patient lift coupled to the gantry and configured to traverse the ceiling grid with the gantry. The modular patient lift system further comprises one or more sensors provided on at least one of the plurality of rails, the gantry, and the patient lift, the one or more sensors configured to collect at least one of environmental data and position data.

In various examples, a modular patient lift system comprises a patient lift configured to couple to a gantry and move within a medical room and one or more sensors provided on the patient lift. The one or more sensors are configured to collect sensed data, wherein the sensed data comprises at least one of environmental data and position data. The modular patient lift system further comprises a controller configured to receive the sensed data and track movement of the patient lift using the received sensed data. The controller is further configured to control one or more of movement of the patient lift or an environmental condition within the medical room based on the received sensed data.

In various examples, a method of controlling a patient lift comprises receiving sensor feedback data, wherein the sensor feedback data comprises environmental data within a medical room and position data relating to a patient lift within the medical room. The method further comprises determining that the sensor feedback data exceeds a threshold and adjusting one or more settings relating to the patient lift based at least in part on the determination that the sensor feedback data exceeds a threshold.

To the accomplishment of the foregoing and related ends, the following description and annexed drawings set forth certain illustrative aspects and implementations. These are indicative of but a few of the various ways in which one or more aspects may be employed. Other aspects, advantages and novel features of the disclosure will become apparent from the following detailed description when considered in conjunction with the annexed drawings.

BRIEF DESCRIPTION OF THE DRAWINGS

The examples disclosed herein may take physical form in certain parts and arrangement of parts, and will be described in detail in this specification and illustrated in the accompanying drawings which form a part hereof and wherein.

DETAILED DESCRIPTION

Figure 1:
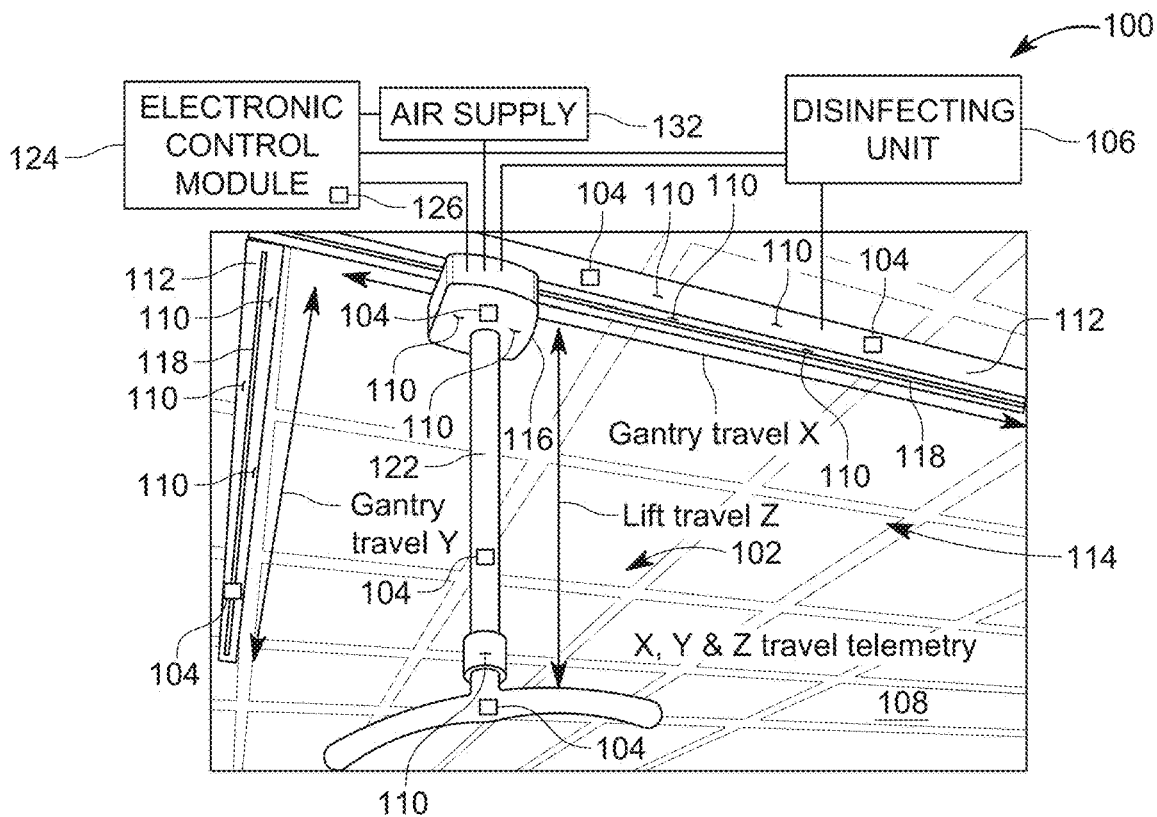
FIG. 1 is a diagram illustrating a patient lift system according to various examples.

The claimed subject matter is now described with reference to the drawings, wherein like reference numerals are generally used to refer to like elements throughout. In the following description, for purposes of explanation, numerous specific details are set forth in order to provide a thorough understanding of the claimed subject matter. It may be evident, however, that the claimed subject matter may be practiced without these specific details. In other instances, structures and devices are shown in block diagram form in order to facilitate describing the claimed subject matter.

Figure 2:
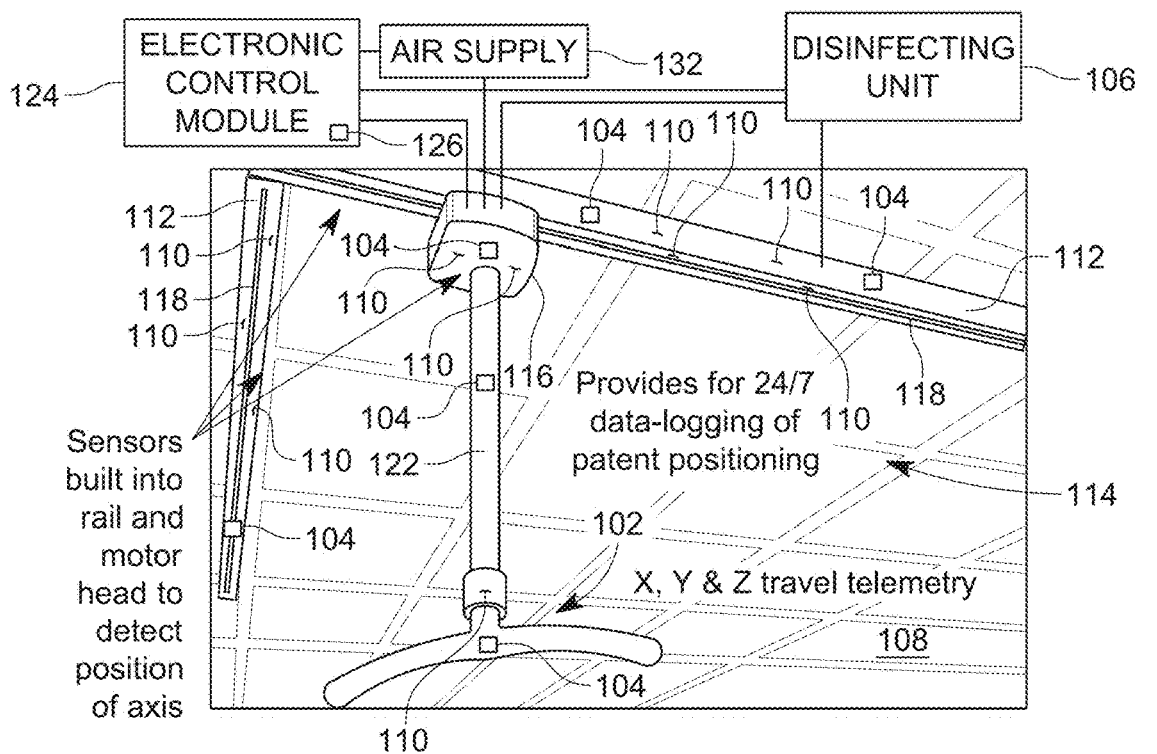
FIG. 2 is another diagram illustrating a patient lift system according to various examples.

Various examples of the present disclosure provide a modular patient lift system 100 as illustrated in FIGS. 1 and 2 that provides electronic movement of a patient lift 102 along an x-axis, y-axis, and z-axis. To enable the electronic movement, the modular patient lift system 100 further includes one or more sensors 104 to provide electronic feedback regarding the position of the patient lift 102 (or a portion thereof) within the x, y, z-axis, such that in one or more examples, a "smart" patient lift 102 is thereby provided. The electronic feedback can include, for example, feedback relating to weight on the patient lift and g-forces of the patient lift. The feedback in various examples is time-stamped to track the movement, location, weight, g-forces, and so forth of the patient lift 102 over time. Additional desired or required feedback are also contemplated by the present disclosure, such as different types of sensing, monitoring, etc.

As described in more detail herein, various examples of the present disclosure further provide one or more of the sensors 104 are configured as environmental sensors on the modular patient lift system 100 that provide environmental feedback on the air quality of the particular area in which the patient lift 102 is located, passes through, and so forth. Some examples further provide a disinfecting unit 106 to provide disinfecting services or operations of the air based on the received feedback from the one or more environmental sensors 104.

As also described in more detail herein, various examples and implementations of the present disclosure enable improved airflow throughout the surgical suite 108 by enabling airflow through the modular patient lift system 100. The modular patient lift system 100 can include vents 110 in rails 112 that used to transport the patient lift 102, a ceiling grid 114 that supports the rails 112 to transport the patient lift 102, and/or the patient lift 102 to enable more efficient airflow to the area in which the patient is located. That is, one or more vents 110 are configured to allow airflow through the particular elements in the modular patient lift system 100, such as from an air supply 132, thereby providing improved airflow to the patient being transported by the modular patient lift system 100 (e.g., providing an environment with improved airflow).

The modular patient lift system 100 in various examples and implementations also provides improved tracking and monitoring, such as of the transport or movement of the patient as described in more detail herein. That is, movement or travel information (e.g., x, y, z telemetry), as well as other information (e.g., other telemetry), relating to the modular patient lift system 100 is tracked or monitored.

It should be noted that the modular patient lift system 100 is for illustration only and should not be construed as limiting. Various examples of the modular patient lift system can be used without departing from the scope of the present disclosure. And variations and modifications are contemplated. For example, the configuration of the vents 110 is shown merely for example. The locations, positions, orientations, size, number, shape, etc. of the vents 110 can be varied as desired or needed, such as based on the configuration of the surgical suite 108 or one or more components therein.

As illustrated in FIG. 1, the modular patient lift system 100 includes the ceiling grid 114 in combination with the plurality of rails 112 that are configured to support a gantry 116 that allows for movable operation of the patient lift 102 along the rails 112. In one example, the ceiling grid 114 provides support for the plurality of rails 112, the gantry 116, a motor (not shown), and the patient lift 102. In some examples, the ceiling grid 114 defines the x-axis and y-axis of the patient lift 102 (e.g., the x and y movement directions of the patient lift 102). The ceiling grid 114 in some examples includes a plurality of tiles and at least one lighting element. Each tile of the plurality of tiles in some examples includes one or more vents configured to facilitate airflow into the space, such as a surgical suite, where the modular patient lift system is implemented. The airflow through the one or more vents can be deployed from a heating, ventilation, and air conditioning (HVAC) system and in some examples can be configured as described, for examples, in U.S. Pat. Nos. 9,903,115, 10,405,942, 11,186,989, and 11,259,893. The lighting element provides at least some of the light for the space and can include, but is not limited to, an incandescent light, a light emitting diode (LED) light, and so forth.

The plurality of rails 112 is supported by the ceiling grid 114. For example, a border provided on at least one side of the ceiling grid 114 supports at least one of the plurality of rails 112. The connection between the plurality of rails 112 and the ceiling, namely the ceiling grid 114, is described in greater detail below in connection with FIGS. 5 and 6. In some examples, the ceiling grid 114 is, forms part of, or is coupled with a modular ceiling system, such as having modular elements that can define different configurations. That is, the modular patient lift system 100 in some examples is incorporated into a modular ceiling system (such as described in U.S. Pat. Nos. 9,903,115 and 11,186,989).

Figure 3:
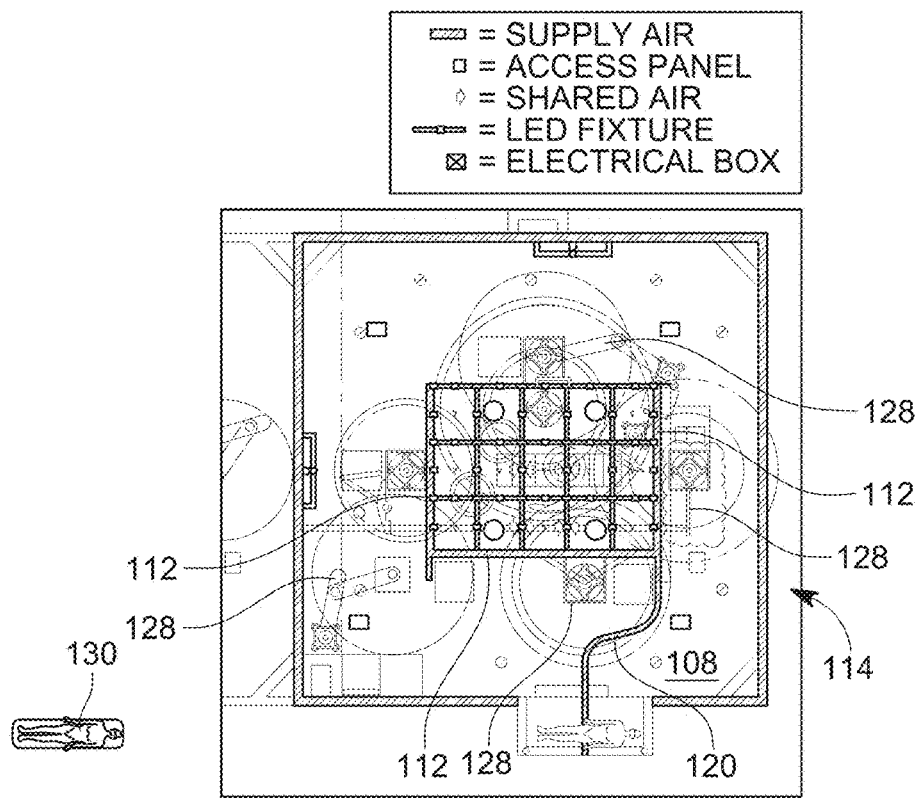
FIG. 3 is a diagram illustrating a medical room in which various examples can be implemented.
Figure 4:
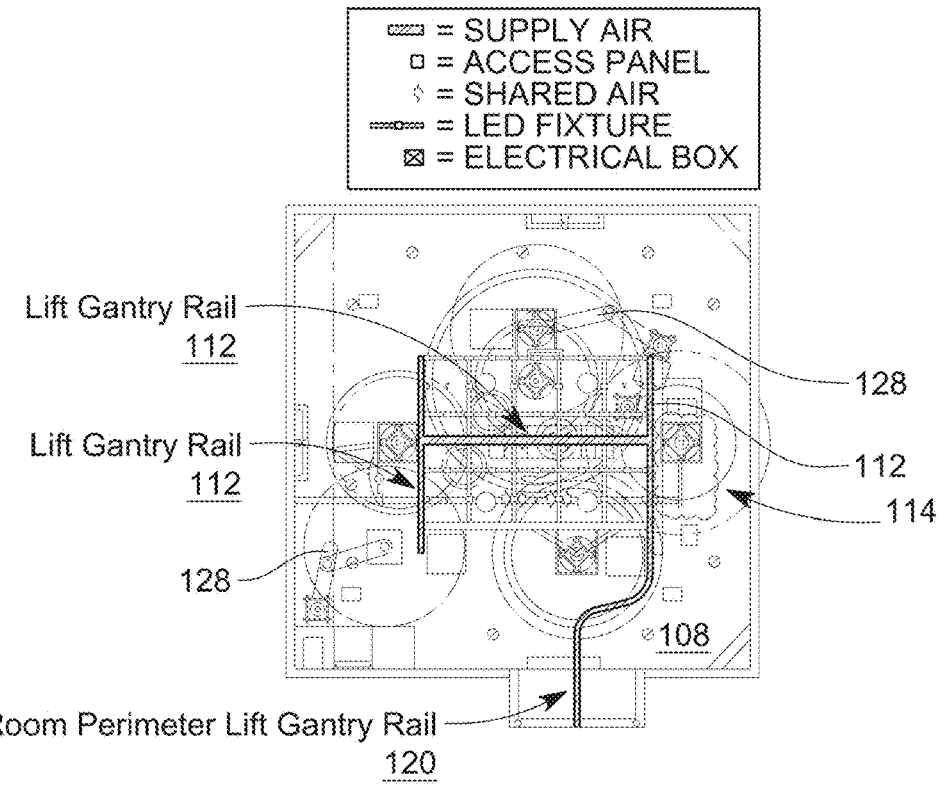
FIG. 4 is another diagram illustrating a medical room in which various examples can be implemented.

In some examples, the plurality of rails 112 include three rails 112 (see also FIGS. 3 and 4). A first rail 112 and a second rail 112 are provided parallel to one another on opposite sides of the ceiling grid 114. The first rail 112 and the second rail 112 can be fixed to the ceiling grid 114. In other words, the first rail 112 and the second rail 112 are not configured to move about the ceiling grid. Each of the first rail 112 and the second rail 112 include a groove 118, or lift channel extrusion, on a face of the rail 112 opposite the ceiling grid 114. For example, as shown in FIGS. 1 and 2, the groove 118 is provided on a face provided downward (lower face) opposite of the ceiling grid 114. However, this example should not be construed as limiting. The term downward is used in relation to the perspective shown in FIGS. 1 and 2 and other examples are possible. As described in greater detail below, one or both of the first rail 112 and the second rail 112 can connect or extend a room perimeter lift gantry rail 120.

A third rail 112 is provided perpendicular to both the first rail 112 and the second rail 112 in some examples. The third rail 112 is configured to move along the first rail 112 and the second rail 112 via the grooves 118 provided in the first rail 112 and the second rail 112. In some examples, the third rail 112 is connected to the groove 118 of the first rail 112 via a first connection mechanism and connected to the groove 118 of the second rail 112 via a second connection mechanism. The first connection mechanism and the second connection mechanism are described in greater detail below. By connecting to the grooves 118 of the first rail 112 and the second rail 112, respectively, the third rail 112 is configured to move back and forth in directions perpendicular to the first rail 112 and the second rail 112, denoted as gantry travel Y in FIG. 1. However, it should be appreciated that other mechanical arrangements and/or configurations to allow movement of the modular patient lift system 100 can be used as desired or needed.

In some examples, the gantry 116 is provided on the third rail 112. More particularly, the gantry 116 is connected to the groove 118 of the third rail 112 via a third connection mechanism. The third connection mechanism enables the gantry 116 to move along the third rail 112, i.e., in a direction perpendicular to each of the first rail 112 and the second rail 112, denoted as gantry travel X in FIG. 1. By combining the movement of the third rail 112 in the gantry travel Y direction and the movement of the gantry 116 along the third rail 112 in the gantry travel X direction, the gantry 116 can traverse an entirety of the area defined by the ceiling grid 114 in some examples.

In some examples, the patient lift 102 is connected to the gantry 116 via a connection mechanism 122 such as a cord, a synthetic rope, a winch, etc. and, accordingly, moves as the gantry 116 is moved. The connection mechanism 122 enables the patient lift 102 to be raised, e.g., moved in a direction toward the ceiling grid 114, by drawing in (e.g., retracting) the connection mechanism 122 and can be lowered, e.g., moved in a direction away from the ceiling grid 114, by letting out (e.g., extending) the connection mechanism 122, denoted by lift travel Z in FIG. 1. When the lift travel Z direction is used in combination with the movement of the gantry 116 and the gantry travel Y direction and the gantry travel X direction, the modular patient lift system 100 includes three-dimensional travel telemetry on an x-axis, a y-axis, and a z-axis as described in more detail herein.

The modular patient lift system 100 further includes at least one motor (not shown). In some examples, a first motor moves the third rail 112, a second motor moves the gantry 116 along the third rail 112, and a third motor draws in and lets out the connection mechanism 122 to raise and lower the patient lift 102. In some examples, the at least one motor is manually controlled by a user to move the patient lift 102. In some examples, the at least one motor is electronically controlled to move the patient lift 102. For example, the at least one motor can be electronically controlled by a controller, such as an electronic control module 124 to traverse the ceiling grid 114. In another example, a specific location including points on each of the x-axis, y-axis, and z-axis on the ceiling grid 114 can be specified, either automatically or by a user input to the electronic control module 124, and the patient lift 102 traverses to the specific location. Any type of motor can be used, such as based on the particular use requirements or application (e.g., maximum weight of a patient, etc.).

Thus, in various examples, the modular patient lift system 100 includes the one or more sensors 104 that provide different telemetry. The one or more sensors 104 can include one or more of sensors 104 provided inside or on the first rail 112, the second rail 112, and/or the third rail 112, one or more sensors 104 provided on the gantry 116, one or more sensors 104 provided on the motor head, and one or more sensors 104 on the patient lift 102, among other locations. The sensors 104 provided inside or on the first rail 112, the second rail 112, and/or the third rail 112 can configured or provided as a sensor 104 that provides feedback data on the specific position of the gantry 116 and the patient lift 102 on the x-axis, y-axis, and z-axis at a particular point in time. The sensors 104 provided inside or on the first rail 112, the second rail 112, and/or the third rail 112 can be individual sensors 104 or provided, for example, on a sensor strip that includes multiple sensors 104. In examples where additional sensors 104 are provided on one or more of the gantry 116, the motor head, and the patient lift 102, the additional sensors 104 provide additional sources of positioning information (or other information) that can be used instead of or in combination with the one or more sensors 104 provided on the plurality of rails 112 to track and log/record the position of the patient lift 102. Accordingly, the one or more sensors 104 provide for twenty-four/seven data logging of positioning of the patient lift 102 and, therefore, positioning of a patient on the patient lift 102. The sensors 104 can be differently positioned or oriented as desired or needed. Different types of sensors 104 can be used and configured to perform monitoring or tracking operations, such as using a potentiometer or other device to measure location or speed, a detector to determine where a pointer is located along a wire, a magnetic detection arrangement, etc. In some examples, sensors 104 can be positioned relative to the ceiling grid 114 at different locations to facilitate patient lift 102 location or speed determinations.

In some examples, the positioning data can be stored in a memory 126 of an electronic device, such as the electronic control module 124. For example, the electronic control module 124 can have various components including, but not limited to, a processor that controls the positioning of the patient lift 102 and a memory 126 that stores the positioning data (and other data). The positioning data can be stored in the memory 126 with accompanying time stamps to identify a particular location or position of the patient lift 102 at a particular time.

In some examples, the one or more sensors 104 further capture additional feedback data regarding one or more of a weight on the patient lift 102, g-forces applied by or on the patient lift 102, and so forth. The feedback data can also be timestamped and stored in the memory 126 of the electronic control module 124. Accordingly, in combination with the positioning data, the timestamped feedback data indicates the time the patient is placed on the patient lift 102, the time the patient is removed from the patient lift 102, the weight on the patient lift 102 when the patient is placed on the lift 102 and the weight on the patient lift 102 when the patient is removed from the patient lift 102, the position of the patient and the patient lift 102 at any particular time, and so forth. In some examples, the timestamped feedback data is used to monitor equipment maintenance feedback. For example, over time, performance of one or more elements of the modular patient lift system 100 can diminish due to wear and tear. In one example, the effectiveness of the one or motors can diminish. This can be measured by comparing the amount of time taken for a particular path by the patient lift 102. An increase in amount of time for the same path to be traversed can indicate a reduced effectiveness of the one or more motors. Based on the feedback of the one or more sensors 104, the electronic control module 124 is configured to output an alert (e.g., a maintenance condition) indicating that equipment maintenance is required to restore initial performance. It should be noted that the feedback data can be used for different purposes (e.g., identify improper use of the patient lift 102, identify potential hazard conditions, etc.) and this is merely an example.

In some examples, the one or more sensors 104 further include one or more environmental feedback sensors 104. For example, one or more environmental feedback sensors 104 can be provided on one or more of the plurality of rails 112, the gantry 116, the motor head, and the patient lift 102. The one or more environmental sensors 104 measure and collect environmental data such as temperature of the air, humidity of the air, airflow volume, airflow speed, particulate counts in the air, the size of particulates in the air, microbial counts in the air, the size of microbials in the air, types of microbials in the air, and so forth. As the patient lift 102 moves throughout the surgical suite via the ceiling grid 114, the environmental feedback sensors 104 collect data regarding the air throughout the surgical suite at particular points in time, which can be periodically, at defined time intervals, continuously, etc. The environmental feedback data is timestamped and stored, such as in the memory 126 of the electronic control module 124.

In some examples, the environmental feedback received from the one or more environmental feedback sensors 104 is compared with previously obtained environmental feedback to monitor the air quality of a space, such as a surgical suite 108, in which the modular patient lift system 100 is implemented. For example, air characteristics can be measured as the patient lift 102 initially moves through the surgical suite 108 to a specified location, such as moving the patient to a procedure table or imaging table, and as the patient lift 102 moves through the surgical suite 108 to the specified location a second time, such as to move the patient from the procedure table or imaging table. Therefore, examples of the present disclosure provide a modular patient lift system 100 that measures and monitors air quality throughout a space, such as a surgical suite 108, over time.

In some examples, as describe herein, the modular patient lift system 100 includes the one or more disinfecting units 106 to disinfect the air in the space. For example, one or more of the gantry 116, motor head, and patient lift 102 includes or is connected to one or more disinfecting units 106 to disinfect air in the location of the patient lift 102 as the patient lift 102 moves through the surgical suite 108. As another example, one or more of the plurality of rails 112 includes or is connected to one or more disinfecting units 106 to disinfect air in the location of the plurality of rails 112. The one or more disinfecting units 106 can include disinfecting elements to disinfect the air by using disinfecting technology including, but not limited to, ultraviolet (UV) light, UVC, Far-UVC, Near UV, 405 nm wavelength light, vaporized hydrogen peroxide (VHP), and so forth. In various examples, the disinfecting unit(s) 106 are activated manually by a user, electronically by a user via the electronic control module 124, or automatically (such as by the electronic control module 124) based on feedback received by the environmental feedback sensors 104. It should be noted that the disinfecting agent can be applied to the air or space in different ways, which in some examples, includes expelling a disinfecting agent through the vents 110 when the disinfecting agent is configured to travel through the air. In other examples, the disinfecting unit(s) 106 are devices or components that emit light to disinfect the air and components within the space, such as the surgical suite 108.

FIGS. 3 and 4 illustrate an example space, such as the surgical suite 108 that includes a plurality of components 128 (e.g., medical imaging components, medical treatment components, medical care components, etc.) and the modular patient lift system 100 according to examples of the present disclosure. The example space illustrated in FIGS. 3 and 4 is for illustration only and should not be construed as limiting. Other examples of the space can be used without departing from the scope of the present disclosure.

In some examples, the space illustrated in FIGS. 3 and 4 that includes the modular patient lift system 100 is a medical setting, such as a surgical suite, a medical imaging room, and so forth. In other examples, the modular patient lift system 100 can be implemented in a non-medical setting and/or for moving objects other than a patient 130. The modular patient lift system, as shown in FIGS. 3 and 4, further includes the room perimeter lift gantry rail 120 in addition to the plurality of rails 112. As can be seen, the room perimeter lift gantry rail 120 extends from outside the entrance and/or exit to the space to the ceiling grid 114. In some examples, the room perimeter lift gantry rail 120 connects to one of the first rail 112 or the second rail 112. In some examples, the room perimeter lift gantry rail 120 is an extension of one of the first rail 112 or the second rail 112. By extending or connecting to one of the first rail 112 or the second rail 112, the room perimeter lift gantry rail 120 enables the gantry 116, motor hear, and patient lift 102 to traverse the space from the entrance to the ceiling grid 114 and from the ceiling grid 114 to the entrance. Accordingly, the patient lift 102 enables the patient 130 to be transported from outside the surgical suite 108 directly to the destination within the surgical suite 108 without an intermediate step of transferring the patient 130. By controlling the modular patient lift system 100 electronically via the electronic control module 124, a precise location for the patient lift 102 within the ceiling grid 114 can be predetermined and the patient 130 can be quickly, precisely, and accurately transported to the destination, can be accurately and precisely tracked, etc.

In some examples, as the patient lift 102 traverses the room perimeter lift gantry rail 120 and the plurality of rails 112, the one or more environmental feedback sensors 104 collect environmental data for particular locations within the space in real time. Based on the collected environmental data, the electronic control module 124 monitors the environmental conditions and adjusts if necessary. For example, the electronic control module 124 adjusts one or more of the temperature of the air, humidity of the air, airflow volume (such as provided by the air supply 132), and airflow speed. In particular, the airflow volume and the airflow speed can be adjusted by adjusting the angle or size of the opening of the plurality of vents 110 included in the modular patient lift system 100. As another example, the electronic control module 124 can affect a change in one or more of the particulate counts in the air, the size of particulates in the air, microbial counts in the air, the size of microbials in the air, types of microbials in the air, and so forth by controlling the one or more disinfecting units 106 described herein. More particularly, the electronic control module 124 controls and adjusts environmental conditions at specific coordinates, identified on the x-axis, y-axis, and z-axis, within the space based on the collected sensor data at the specific coordinates. It should be noted that the modular patient lift system 100 can control other factors or operations in response to the received feedback from the sensors 104, such as the speed of the patient lift 102, the height of the patient lift 102, the direction of travel of the patient lift 102, etc.

Figure 5:
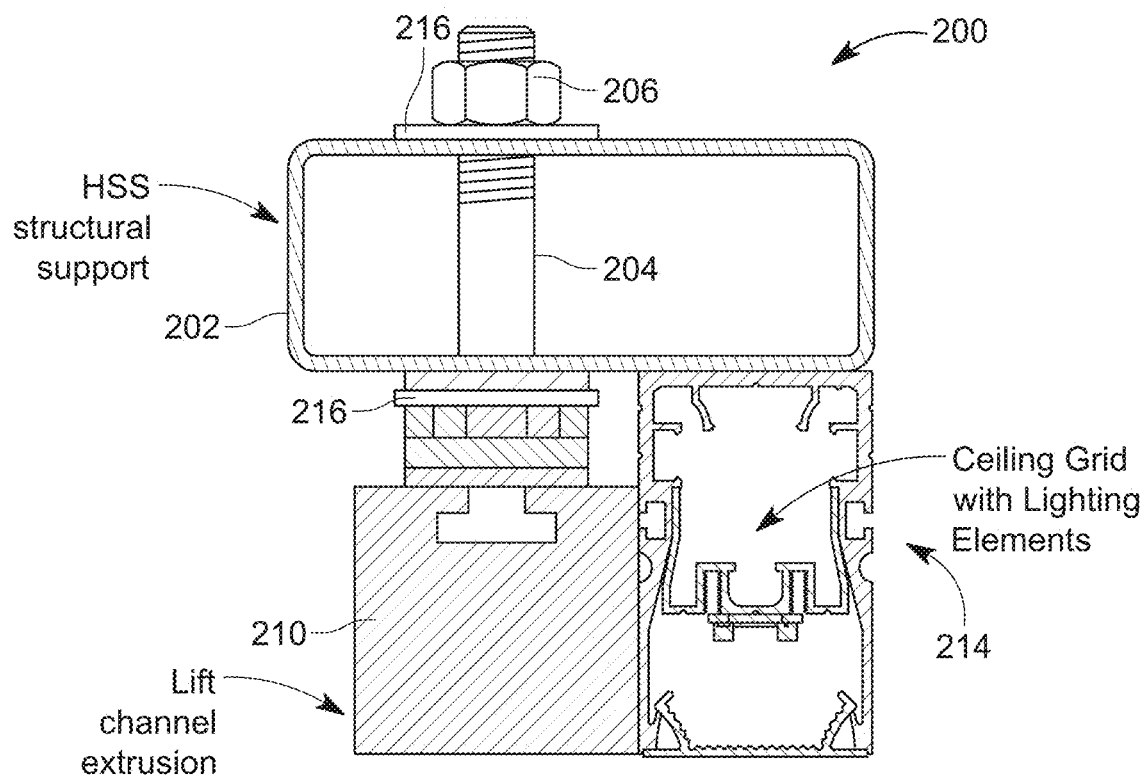
FIG. 5 is a diagram illustrating a mounting arrangement according to various examples.
Figure 6:
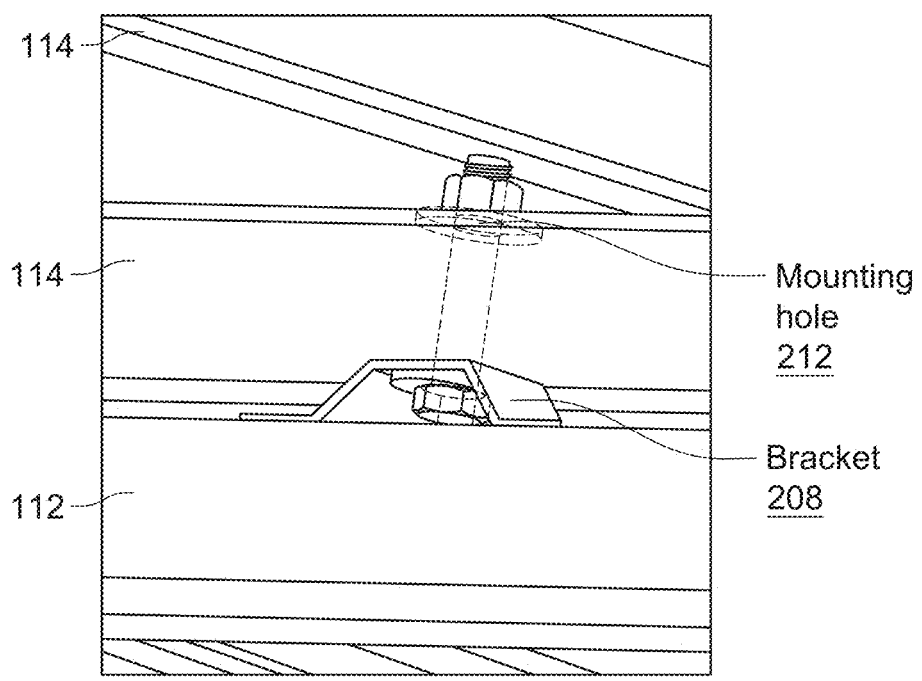
FIG. 6 is a diagram illustrating a bracket arrangement according to various examples.

FIGS. 5 and 6 illustrate a mounting arrangement 200 that allows for coupling one or more of the plurality of rails 112 to the ceiling grid 114. More particularly, FIG. 5 illustrates a cross-section of the mounting arrangement 200 and FIG. 6 illustrates the rail 112 coupled to the ceiling grid 114 via the mounting arrangement 200. The mounting arrangement 200 illustrated in FIGS. 5 and 6 is for illustration only and should not be construed as limiting. Other examples of the mounting arrangement 200 can be used without departing from the scope of the present disclosure. It should be noted that the rail 112 illustrated in FIGS. 5 and 6 can be any of the plurality of rails 112 described herein.

The mounting arrangement 200 includes a hollow structural section (HSS) structural support 202, a fastening arrangement including a bolt 204 and a nut 206, a bracket 208, and a lift channel extrusion 210. The HSS structural support 202 is various examples is included in a portion of the ceiling grid 114 and provides a connection point between the ceiling grid 114 and the rail 112. As illustrated in FIG. 6, a mounting hole 212 is provided in the HSS structural support 202 to allow the bolt 204 to extend through the HSS structural support 202 to the rail 114. The bracket 208, as illustrated in FIG. 6, is provided (e.g., coupled to, integrated as part of) on a portion of the rail 112 proximate to the ceiling grid 114. The bolt 204 extends from the bracket 208 through the HSS structural support 202 and is fastened with the nut 206 above the HSS structural support 202. In some examples, at least one washer 216 is provided between the nut 206 and the HSS structural support 202 and/or between the head of the bolt 204 and the bracket 208.

On the rail 112, opposite the bracket 208, e.g., on the bottom of the rail 112, is the groove 118, also referred to as a lift channel extrusion. When implemented in the first rail 112 or the second rail 112, the groove 118 enables the third rail 112 to traverse the ceiling grid 114 and when implemented in the third rail 112, the groove 118 enables the gantry 116 to thereby traverse the ceiling grid 114.

As shown in FIG. 5, the mounting arrangement 200 can be provided proximate to a lighting element arrangement 214 of the ceiling grid 114. The lighting element arrangement 214 can be provided in different ways and configuration, and in some examples, is provided, for example, as described in one or more of U.S. Pat. Nos. 9,903,115, 10,405,942, and 11,259,893. In some examples, multiple HSS structural supports 202 can be formed in a grid to define the ceiling grid 114 and form a border for individual lighting element arrangements 214, which provides at least some of the light for the medical setting. As described herein, the lighting element arrangement 214 can includes an incandescent light, an LED light, and so forth.

Although described herein as a single mount, it should be understood that multiple mounts such as the mounting arrangement 200 illustrated in FIGS. 5 and 6 are used in combination to mount the plurality of rails 112 to the ceiling grid 114. In other words, each rail 112 of the plurality of rails 112 is coupled to the ceiling grid 114 via multiple mounting arrangements 200 described herein.

In some examples, the present disclosure can be implemented with co-pending application having application Ser. No. 63/190,238 entitled "Modular Return Air Device" and with co-pending application having application Ser. No. 63/190,241 entitled "Central Medical Suite System", and with co-pending application Ser. No. 17/529,010 and co-pending application Ser. No. 17/694,377; and with U.S. Pat. Nos. 9,671,100, 9,895,202, 9,903,115, and U.S. Pat. No. 10,405,942.

Figure 7:
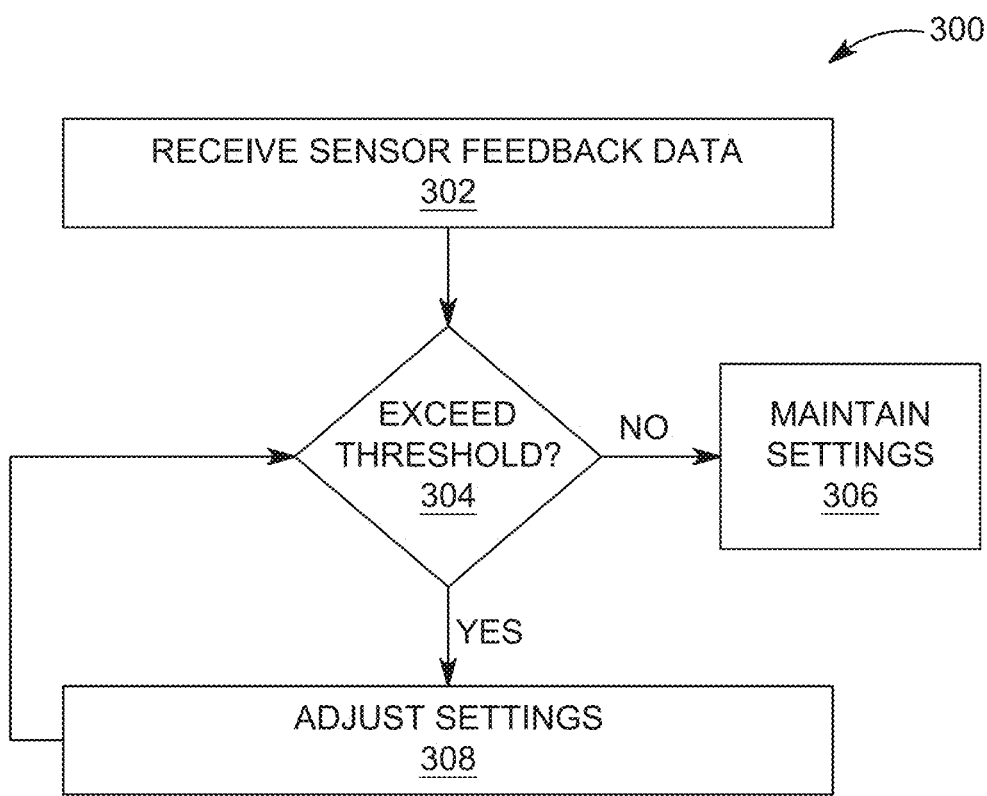
FIG. 7 illustrates an example of a method for generating one or more control signals for controlling a patient lift system according to various examples.

The electronic control module 124 in various examples is configured to monitor and/or control the patient lift system 100, as illustrated in the flowchart 300 of FIG. 7. For example, the electronic control module 124 in some examples is operable to generate one or more control signals to control one or more components, operations, etc. of the patient lift system 100. That is, in one or more examples, the flowchart 300 illustrates operations involved in generating one or more control signals for controlling movement of the patient lift 102 and/or airflow provided by the modular patient lift system 100. In some examples, the operations of the flowchart 300 generate signals to control operation of the patient lift 102, gantry 116, air flow from the air supply 132 through the vents 110, the disinfecting unit 106, etc. as described herein. The flowchart 300 commences at operation 302 with receiving sensor feedback data. For example, the electronic control module 124 receives measurements, sensed data, etc. from one or more of the sensors 104 as described in more detail herein. A determination is then made at 304 whether the received data, exceeds a threshold at 304. For example, a determination is made whether the measurements exceed an air quality level, a speed level, etc. It should be noted that different threshold levels or values can be defined for different operating conditions, different patients 130, different surgical suites 108, etc. That is, the thresholds in some examples are defined to monitor or control operations and/or conditions relating to a particular configuration or setting.

If a determination is made that none of the one or more thresholds is exceeded, the settings for the various operations are maintained at 306. That is, the settings for the operation of the modular patient lift system 100, such as speed, airflow, etc. are maintained at a current level or state at 306. If a determination is made that one or more of the thresholds is exceeded, then one or more settings are adjusted at 308. For example, a speed, airflow, amount of sanitizing, etc. are adjusted at 308. The adjustment can include an increase or decrease is in one or more settings.

Thus, one or more examples provide a patient lift system with improved operation. For example, improved control and/or monitoring is provided by various examples.

Figure 8:
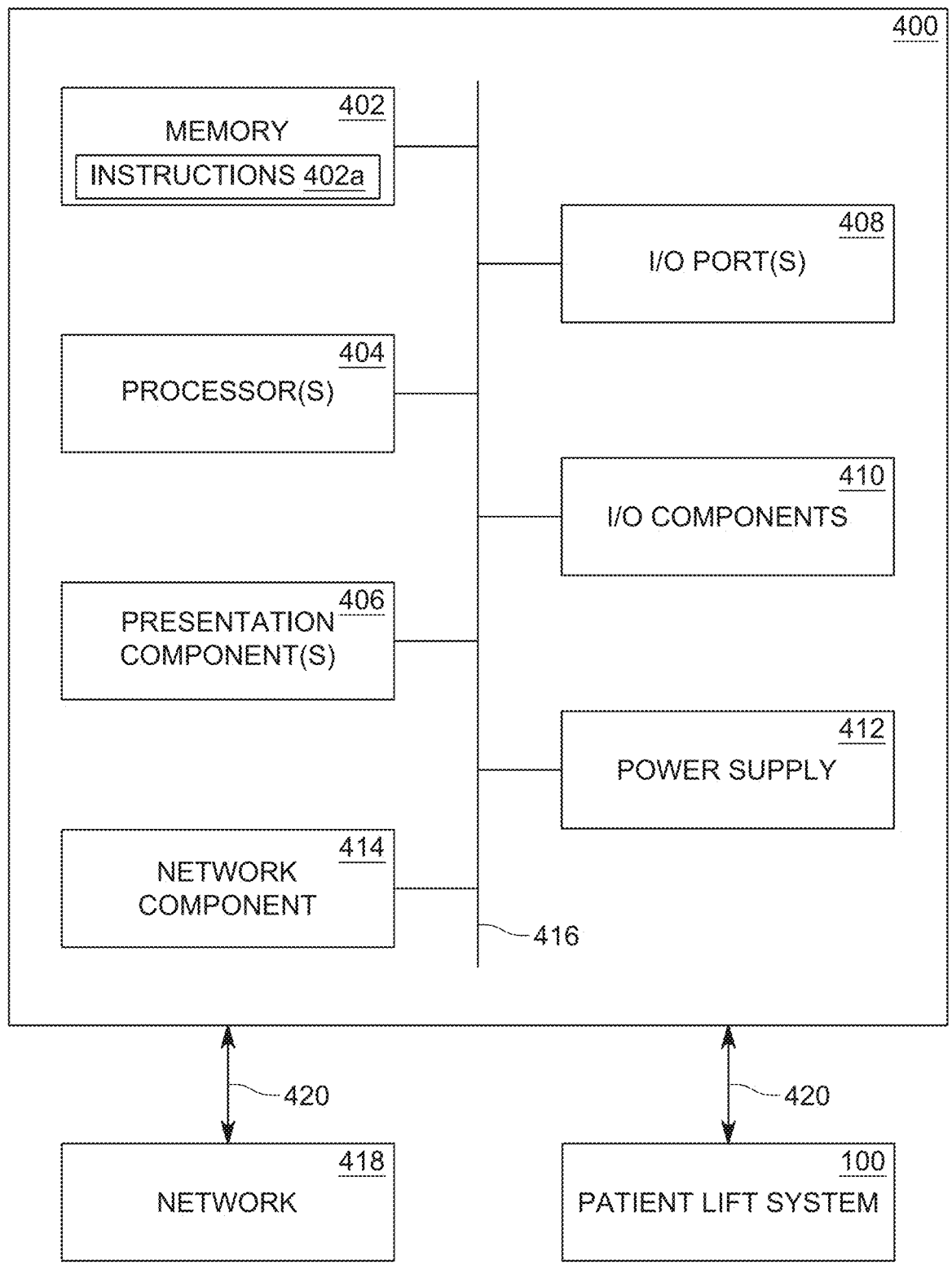
FIG. 8 is a block diagram of a computing environment suitable for implementing various examples.

With reference now to FIG. 8, a block diagram of a computing device 400 suitable for implementing various aspects of the disclosure as described (e.g., operations or functions to control the modular patient lift system 100). FIG. 8 and the following discussion provide a brief, general description of a computing environment in/on which one or more or the implementations of one or more of the methods and/or system set forth herein may be implemented. The operating environment of FIG. 8 is merely an example of a suitable operating environment and is not intended to suggest any limitation as to the scope of use or functionality of the operating environment. Example computing devices include, but are not limited to, personal computers, server computers, hand-held or laptop devices, mobile devices (such as mobile phones, mobile consoles, tablets, media players, and the like), multiprocessor systems, consumer electronics, mini computers, mainframe computers, distributed computing environments that include any of the above systems or devices, and the like.

Although not required, implementations are described in the general context of "computer readable instructions" executed by one or more computing devices. Computer readable instructions may be distributed via computer readable media (discussed below). Computer readable instructions may be implemented as program modules, such as functions, objects, Application Programming Interfaces (APIs), data structures, and the like, that perform particular tasks or implement particular abstract data types. Typically, the functionality of the computer readable instructions may be combined or distributed as desired in various environments.

In some examples, the computing device 400 includes a memory 402, one or more processors 404, and one or more presentation components 406. The disclosed examples associated with the computing device 400 are practiced by a variety of computing devices, including personal computers, laptops, smart phones, mobile tablets, hand-held devices, consumer electronics, specialty computing devices, etc. Distinction is not made between such categories as "workstation," "server," "laptop," "hand-held device," etc., as all are contemplated within the scope of FIG. 8 and the references herein to a "computing device." The disclosed examples are also practiced in distributed computing environments, where tasks are performed by remote-processing devices that are linked through a communications network. Further, while the computing device 400 is depicted as a single device, in one example, multiple computing devices work together and share the depicted device resources. For instance, in one example, the memory 402 is distributed across multiple devices, the processor(s) 404 provided are housed on different devices, and so on.

In one example, the memory 402 includes any of the computer-readable media discussed herein. In one example, the memory 402 is used to store and access instructions 402*a* configured to carry out the various operations disclosed herein. In some examples, the memory 402 includes computer storage media in the form of volatile and/or nonvolatile memory, removable or non-removable memory, data disks in virtual environments, or a combination thereof. In one example, the processor(s) 404 includes any quantity of processing units that read data from various entities, such as the memory 402 or input/output (I/O) components 410. Specifically, the processor(s) 404 are programmed to execute computer-executable instructions for implementing aspects of the disclosure. In one example, the instructions 402*a* are performed by the processor 404, by multiple processors within the computing device 400, or by a processor external to the computing device 400. In some examples, the processor(s) 404 are programmed to execute instructions such as those illustrated in the flow charts discussed herein and depicted in the accompanying drawings.

In other implementations, the computing device 400 may include additional features and/or functionality. For example, the computing device 400 may also include additional storage (e.g., removable and/or non-removable) including, but not limited to, magnetic storage, optical storage, and the like. Such additional storage is illustrated in FIG. 8 by the memory 402. In one implementation, computer readable instructions to implement one or more implementations provided herein may be in the memory 402 as described herein. The memory 402 may also store other computer readable instructions to implement an operating system, an application program and the like. Computer readable instructions may be loaded in the memory 402 for execution by the processor(s) 404, for example.

The presentation component(s) 406 present data indications to an operator or to another device. In one example, the presentation components 406 include a display device, speaker, printing component, vibrating component, etc. One skilled in the art will understand and appreciate that computer data is presented in a number of ways, such as visually in a graphical user interface (GUI), audibly through speakers, wirelessly between the computing device 400, across a wired connection, or in other ways. In one example, the presentation component(s) 406 are not used when processes and operations are sufficiently automated that a need for human interaction is lessened or not needed. I/O ports 408 allow the computing device 400 to be logically coupled to other devices including the I/O components 410, some of which is built in. Implementations of the I/O components 410 include, for example but without limitation, a microphone, keyboard, mouse, joystick, pen, game pad, satellite dish, scanner, printer, wireless device, camera, etc.

The computing device 400 includes a bus 416 that directly or indirectly couples the following devices: the memory 402, the one or more processors 404, the one or more presentation components 406, the input/output (I/O) ports 408, the I/O components 410, a power supply 412, and a network component 414. The computing device 400 should not be interpreted as having any dependency or requirement related to any single component or combination of components illustrated therein. The bus 416 represents one or more busses (such as an address bus, data bus, or a combination thereof). Although the various blocks of FIG. 8 are shown with lines for the sake of clarity, some implementations blur functionality over various different components described herein.

The components of the computing device 400 may be connected by various interconnects. Such interconnects may include a Peripheral Component Interconnect (PCI), such as PCI Express, a Universal Serial Bus (USB), firewire (IEEE 1394), an optical bus structure, and the like. In another implementation, components of the computing device 400 may be interconnected by a network. For example, the memory 602 may be comprised of multiple physical memory units located in different physical locations interconnected by a network.

In some examples, the computing device 600 is communicatively coupled to a network 618 using the network component 414. In some examples, the network component 414 includes a network interface card and/or computer-executable instructions (e.g., a driver) for operating the network interface card. In one example, communication between the computing device 400 and other devices occurs using any protocol or mechanism over a wired or wireless connection 420. In some examples, the network component 414 is operable to communicate data over public, private, or hybrid (public and private) connections using a transfer protocol, between devices wirelessly using short range communication technologies (e.g., near-field communication (NFC), Bluetooth® branded communications, or the like), or a combination thereof.

The connection 420 may include, but is not limited to, a modem, a Network Interface Card (NIC), an integrated network interface, a radio frequency transmitter/receiver, an infrared port, a USB connection or other interfaces for connecting the computing device 400 to other computing devices. The connection 420 may transmit and/or receive communication media. In some examples, the connection 420 allows communication with the modular patient lift system 100 to allow, for example, for adjustment of the operation thereof.

Although described in connection with the computing device 400, examples of the disclosure are capable of implementation with numerous other general-purpose or special-purpose computing system environments, configurations, or devices. Implementations of well-known computing systems, environments, and/or configurations that are suitable for use with aspects of the disclosure include, but are not limited to, smart phones, mobile tablets, mobile computing devices, personal computers, server computers, hand-held or laptop devices, multiprocessor systems, gaming consoles, microprocessor-based systems, set top boxes, programmable consumer electronics, mobile telephones, mobile computing and/or communication devices in wearable or accessory form factors (e.g., watches, glasses, headsets, or earphones), network PCs, minicomputers, mainframe computers, distributed computing environments that include any of the above systems or devices, VR devices, holographic device, and the like. Such systems or devices accept input from the user in any way, including from input devices such as a keyboard or pointing device, via gesture input, proximity input (such as by hovering), and/or via voice input.

Implementations of the disclosure, such as controllers or monitors, are described in the general context of computer-executable instructions, such as program modules, executed by one or more computers or other devices in software, firmware, hardware, or a combination thereof. In one example, the computer-executable instructions are organized into one or more computer-executable components or modules. Generally, program modules include, but are not limited to, routines, programs, objects, components, and data structures that perform particular tasks or implement particular abstract data types. In one example, aspects of the disclosure are implemented with any number and organization of such components or modules. For example, aspects of the disclosure are not limited to the specific computer-executable instructions or the specific components or modules illustrated in the figures and described herein. Other examples of the disclosure include different computer-executable instructions or components having more or less functionality than illustrated and described herein. In implementations involving a general-purpose computer, aspects of the disclosure transform the general-purpose computer into a special-purpose computing device when configured to execute the instructions described herein.

By way of example and not limitation, computer readable media comprises computer storage media and communication media. Computer storage media include volatile and nonvolatile, removable, and non-removable memory implemented in any method or technology for storage of information such as computer readable instructions, data structures, program modules, or the like. Computer storage media are tangible and mutually exclusive to communication media. Computer storage media are implemented in hardware and exclude carrier waves and propagated signals. Computer storage media for purposes of this disclosure are not signals per se. In one example, computer storage media include hard disks, flash drives, solid-state memory, phase change random-access memory (PRAM), static random-access memory (SRAM), dynamic random-access memory (DRAM), other types of random-access memory (RAM), read-only memory (ROM), electrically erasable programmable read-only memory (EEPROM), flash memory or other memory technology, compact disk read-only memory (CD-ROM), digital versatile disks (DVD) or other optical storage, magnetic cassettes, magnetic tape, magnetic disk storage or other magnetic storage devices, or any other non-transmission medium used to store information for access by a computing device. In contrast, communication media typically embody computer readable instructions, data structures, program modules, or the like in a modulated data signal such as a carrier wave or other transport mechanism and include any information delivery media.

While various spatial and directional terms, including but not limited to top, bottom, lower, mid, lateral, horizontal, vertical, front and the like are used to describe the present disclosure, it is understood that such terms are merely used with respect to the orientations shown in the drawings. The orientations can be inverted, rotated, or otherwise changed, such that an upper portion is a lower portion, and vice versa, horizontal becomes vertical, and the like.

The word "exemplary" is used herein to mean serving as an example, instance or illustration. Any aspect or design described herein as "exemplary" is not necessarily to be construed as advantageous over other aspects or designs. Rather, use of the word exemplary is intended to present concepts in a concrete fashion. As used in this application, the term "or" is intended to mean an inclusive "or" rather than an exclusive "or." That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. Further, at least one of A and B and/or the like generally means A or B or both A and B. In addition, the articles "a" and "an" as used in this application and the appended claims may generally be construed to mean "one or more" unless specified otherwise or clear from context to be directed to a singular form.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims. Of course, those skilled in the art will recognize many modifications may be made to this configuration without departing from the scope or spirit of the claimed subject matter.

As used herein, a structure, limitation, or element that is "configured to" perform a task or operation is particularly structurally formed, constructed, or adapted in a manner corresponding to the task or operation. For purposes of clarity and the avoidance of doubt, an object that is merely capable of being modified to perform the task or operation is not "configured to" perform the task or operation as used herein.

Various operations of implementations are provided herein. In one implementation, one or more of the operations described may constitute computer readable instructions stored on one or more computer readable media, which if executed by a computing device, will cause the computing device to perform the operations described. The order in which some or all of the operations are described should not be construed as to imply that these operations are necessarily order dependent. Alternative ordering will be appreciated by one skilled in the art having the benefit of this description. Further, it will be understood that not all operations are necessarily present in each implementation provided herein.

Any range or value given herein can be extended or altered without losing the effect sought, as will be apparent to the skilled person.

Also, although the disclosure has been shown and described with respect to one or more implementations, equivalent alterations and modifications will occur to others skilled in the art based upon a reading and understanding of this specification and the annexed drawings. The disclosure includes all such modifications and alterations and is limited only by the scope of the following claims. In particular regard to the various functions performed by the above described components (e.g., elements, resources, etc.), the terms used to describe such components are intended to correspond, unless otherwise indicated, to any component which performs the specified function of the described component (e.g., that is functionally equivalent), even though not structurally equivalent to the disclosed structure which performs the function in the herein illustrated exemplary implementations of the disclosure.

Although examples described herein are described in connection with a particular air handling arrangement and environment, the present disclosure can be implemented in different arrangements and in different environments. For example, the present disclosure is implementable in any application or environment in which air flow control is desired.

As used in this application, the terms "component," "module," "system," "interface," and the like are generally intended to refer to a computer-related entity, either hardware, a combination of hardware and software, software, or software in execution. For example, a component may be, but is not limited to being, a process running on a processor, a processor, an object, an executable, a thread of execution, a program and/or a computer. By way of illustration, both an application running on a controller and the controller can be a component. One or more components may reside within a process and/or thread of execution and a component may be localized on one computer and/or distributed between two or more computers.

Furthermore, the claimed subject matter may be implemented as a method, apparatus or article of manufacture using standard programming and/or engineering techniques to produce software, firmware, hardware or any combination thereof to control a computer to implement the disclosed subject matter. The term "article of manufacture" as used herein is intended to encompass a computer program accessible from any computer-readable device, carrier or media. Of course, those skilled in the art will recognize many modifications may be made to this configuration without departing from the scope or spirit of the claimed subject matter.

In addition, while a particular feature of the disclosure may have been disclosed with respect to only one of several implementations, such feature may be combined with one or more other features of the other implementations as may be desired and advantageous for any given or particular application. Furthermore, to the extent that the terms "includes," "having," "has," "with," or variants thereof are used in either the detailed description or the claims, such terms are intended to be inclusive in a manner similar to the term "comprising."

The implementations have been described, hereinabove. It will be apparent to those skilled in the art that the above methods and apparatuses may incorporate changes and modifications without departing from the general scope of this invention. It is intended to include all such modifications and alterations in so far as they come within the scope of the appended claims or the equivalents thereof.

What is claimed is:

1. A modular patient lift system, comprising:
    a ceiling grid;
    a plurality of rails;
    a gantry configured to traverse the ceiling grid via the plurality of rails;
    a patient lift coupled to the gantry and configured to traverse the ceiling grid with the gantry;
    one or more sensors provided on at least one of the plurality of rails, the gantry, and the patient lift, the one or more sensors configured to collect at least one of environmental data and position data; and
    a plurality of vents provided in the gantry and the patient lift, the plurality of vents configured to allow airflow therethrough.

2. The modular patient lift system of claim 1, wherein the plurality of vents are further provided in the plurality of rails.

3. The modular patient lift system of claim 1, further comprising an electronic control module configured to control the airflow.

4. The modular patient lift system of claim 1, further comprising an electronic control module configured to control a movement of at least one of the gantry and a rail of the plurality of rails.

5. The modular patient lift system of claim 1, further comprising one or more disinfecting units provided on or in connection with at least one of the plurality of rails, the gantry, and the patient lift.

6. The modular patient lift system of claim 5, further comprising an electronic control module configured to control the one or more disinfecting units.

7. The modular patient lift system of claim 1, wherein the position data comprises one or more of x-direction travel telemetry, y-direction travel telemetry, and z-direction travel telemetry.

8. The modular patient lift system of claim 1, further comprising an electronic control module configured to track patient movement based on movement of the patient lift.

9. The modular patient lift system of claim 1, wherein the collected position data comprises speed data and further comprising an electronic control module configured to determine a maintenance condition based on the collected speed data.

10. The modular patient lift system of claim 1, wherein the collected environmental data comprises one or more air quality measurement data.

11. The modular patient lift system of claim 1, wherein the plurality or rails comprise one or more brackets configured to mount to the ceiling grid in combination with a lighting element arrangement.

12. A modular patient lift system, comprising:
    a patient lift configured to couple to a gantry and move within a medical room;
    one or more sensors provided on the patient lift, the one or more sensors configured to collect sensed data, wherein the sensed data comprises at least one of environmental data and position data, wherein the position data comprises a plurality of coordinates; and
    a controller configured to receive the sensed data and track movement of the patient lift using the received sensed data, the controller further configured to control movement of the patient lift and an environmental condition within the medical room based on the received sensed data, wherein controlling the environmental condition comprises adjusting the environmental condition at a location of the patient lift defined by the plurality of coordinates and based on the sensed data at the location.

13. The modular patient lift system of claim 12, further comprising a plurality of vents provided at least one of the gantry and the patient lift, the plurality of vents configured to allow airflow therethrough, wherein the controller is further configured to control the airflow based at least in part on the received sensed data.

14. The modular patient lift system of claim 12, further comprising one or more disinfecting units provided on or in connection with at least one of the gantry and the patient lift, wherein the controller is further configured to control disinfection by the one or more disinfecting units based at least in part on the received sensed data.

15. The modular patient lift system of claim 12, wherein the position data comprises one or more of x-direction travel telemetry, y-direction travel telemetry, and z-direction travel telemetry.

16. The modular patient lift system of claim 12, wherein the position data comprises speed data and the controller is configured to determine a maintenance condition based on the speed data.

17. The modular patient lift system of claim 12, wherein the position data comprises speed data and the controller is configured to determine a safety condition based on the speed data.

18. The modular patient lift system of claim 12, wherein the environmental data comprises one or more environmental measurements within the medical room and the controller is configured to determine an environmental condition based on the one or more environmental measurements.

19. A modular patient lift system, comprising:
    a ceiling grid forming part of a modular ceiling system, the ceiling grid comprising a border on at least one side of the ceiling grid;
    a plurality of rails supported by the ceiling grid;
    a gantry coupled with the modular ceiling system and configured to traverse the ceiling grid along one or more rails of the plurality of rails;
    a patient lift coupled to the gantry and configured to traverse the ceiling grid with the gantry; and a plurality of vents provided in the gantry and the patient lift, the plurality of vents configured to allow airflow therethrough,
wherein the border supports at least one of the plurality of rails.

* * * * *